United States Patent [19]

Rheinberger et al.

[11] Patent Number: 5,383,752
[45] Date of Patent: Jan. 24, 1995

[54] APPARATUS FOR MAKING DENTAL REPLACEMENTS

[75] Inventors: Volker M. Rheinberger, Vaduz, Switzerland; Gary Unterbrink, Feldkirch, Australia; Cosmas Malin, Mauren; Harry L. Sawatzki, Schaan, both of Switzerland

[73] Assignee: Liconic AG, Mauren, Liechtenstein

[21] Appl. No.: 977,035

[22] Filed: Nov. 16, 1992

[30] Foreign Application Priority Data

Nov. 17, 1991 [CH] Switzerland ............... 3-357/91

[51] Int. Cl.⁶ ............... B23C 3/00; A61C 5/10
[52] U.S. Cl. ............... 409/105; 128/776; 409/104; 409/111; 433/223
[58] Field of Search ............... 29/33 R; 433/223, 204, 433/76; 409/111, 105, 106, 112, 104, 114, 126, 80; 128/776

[56] References Cited

U.S. PATENT DOCUMENTS

| | | | |
|---|---|---|---|
| 2,330,566 | 9/1943 | Edmunds et al. | 409/111 |
| 2,539,027 | 1/1951 | Marchant | 409/126 X |
| 2,793,569 | 5/1957 | Tanner et al. | 433/76 |
| 4,411,626 | 10/1983 | Becker et al. | 433/223 |
| 4,575,805 | 3/1986 | Moermann et al. | 128/776 X |
| 4,937,928 | 7/1990 | van der Zel | 29/160.6 |

FOREIGN PATENT DOCUMENTS 8706451 11/1987 WIPO ............... 433/223

*Primary Examiner*—William Briggs

[57] ABSTRACT

The method described in this disclosure permits the production of dental replacements, such as inlays, onlays, and crowns, at high accuracy of fit and low cost in a single session of the patient's at the dentist's. For this purpose, a material that hardens is used for making a temporary inlay which provides an impression of the prepared dental cavity. After hardening, this material is removed from the tooth. In a first processing run, a first sensor (7a) does a preliminary scan of the temporary inlay (4) and a first processing tool (30a) is used for preliminary processing of the substrate mass (6). In a second processing run a second sensor (7b) and a second processing tool (30b) are used for a fine scan and fine processing. For this purpose the sensors (7a, 7b) and the processing tools (30a, 30b) are all arranged on a single linear stage (13). The temporary inlay (4) and the substrate mass (6) are attached to holder units (3, 5) of a rotation-synchronizer system (10) which in turn is arranged on a slide and elevator system (11, 12).

22 Claims, 10 Drawing Sheets

APPARATUS FOR MAKING DENTAL REPLACEMENTS

BACKGROUND OF THE INVENTION

The present invention relates to a method of making dental replacements, in particular inlays, onlays, and crowns, and to an apparatus for implementing said method, wherein a template is made, the template is scanned by means of at least one sensor, and the scanning movements are transmitted to at least one processing tool, so that a dental replacement whose shape corresponds to that of the template can be made from a blank in the form of a substrate mass.

Most dental fillings are at present made of amalgam. The reasons are their long life, low cost, and the fact that they can be made and fitted in a single session of the patient's at the dentist's. The main disadvantages are the low aesthetic worth of amalgam fillings and the fact that the health aspects of the materials used in their manufacture are no longer undisputed.

The known alternatives are gold fillings, composites, inlays, and onlays. Of these, composites are suitable only for fairly small replacements. Gold fillings or inlays are available for larger replacements. Because metal fillings are expensive and their colour cannot be matched with that of the natural tooth, they are being increasingly superseded by inlays and onlays made of resistant synthetic or ceramic materials whose colour can be matched with that of the tooth. They are produced by means of a template made in the patient's mouth. The classic procedure for the production of the so-called dental technician's ceramic inlays and onlays is to make a negative template. The inlay or onlay itself is made by means of this negative template, by a series of steps in which it is fitted. The accuracy of fit of these dental technician's inlays and onlays can be improved by increasing the number of steps of firing. This method is expensive and, in particular, requires the patient to have two sessions at the dentist's. Because of this, other methods have been developed that attempt to make it possible to produce an inlay or onlay filling in a single session. The factor common to all these methods is that they make use of a mobile processing tool that produces, the inlay or onlay directly from a blank by cutting milling, and grinding.

EP-B-0 182 098 describes such a method, in which the information for the control of the processing tool is computed from an image of the prepared tooth projected on a monitor and by manual input of the section line on the monitor. After data acquisition, the processing tool makes use of the computed data to shape the inlay or onlay by combined movements. An all three axes. This method permits inlay fillings to be made relatively quickly. But the accuracy of fit is unsatisfactory for several basic reasons. Firstly, local optical resolution and the imaging properties of the projected image cannot be of the required quality because the size of the device is necessarily small. Secondly, the connection of the manually input coordinates for the shape of the tooth is only approximate and can lead to errors in the computation of the outline-of the side walls in the prepared tooth. A further source of error is the manual input of the section line itself, because it leaves a large margin of discretion to the operator. Also, because optical means are used to measure the prepared cavity, the shape of the cavity is subject to considerable restraints, it demands the removal of unnecessary amounts of healthy dental material during preparation, and requires the dentist to learn and observe special procedures in preparing the cavity. A particular disadvantage of this method has proved to be the fact that especially large errors occur precisely in the least accessible places. Further, this method does not permit the direct shaping of the tooth's masticatory surface. Finally, the equipment based on this method is complex to make and very expensive.

EP-A-0 402 720 describes another method. As in the case of the dental technician's inlay/onlay, this makes use of a template prepared in the patient's mouth. The template is held in a movable mount and scanned by a manually controlled, likewise movable scanning head, until it has touched all the points on the template's surface. The mechanical connection of the processing tool to the scanning head is such that it copies the scanning head's movements. For the visualization of the places that the scanning head has touched, a dye that reacts to contact is applied to the template. In theory, when sufficiently fine processing tools are used in this method, it permits the production of inlays and onlays that fit accurately. In practice, this method has many drawbacks. While manual scanning is performed, the milling tool must at the same time be guided through the material of the substrate mass. The amount of force that this demands causes the loss of the requisite sensitivity for a precise scan of the template. For the scanning process, the template must be held in a somewhat unstable manner between pointed tips. Apart from deformations due to this type of support, cumulative errors occur in the pointed tips, the points of contact between the tips and the template, and in the template itself, because of inadequate control of the contact pressure used in scanning. Particularly when large amounts of material have to be removed, slight prominences and depressions in the surface form and texture become blurred. Unless special care is taken to fit the temporary inlay in the mount or if the shape of the template does not allow the mount to provide adequate support, the temporary inlay used as a template may shift between the tips of the mount that hold it in place.

To keep errors due to elastic deformation as small as possible when a pointed tool is used, the template must be made of hard material. But a template of hard material is more difficult to secure in the machine. The most serious difficulties due to the use of hard filling material are the problems that arise when the template is removed from the tooth. For example, because it closely fits the tooth, the temporary inlay is difficult to remove. If there is undercutting in the preparation of the cavity, removal of the complete temporary inlay becomes impossible without permanent damage to the tooth, and the tooth has to be prepared again under aggravated conditions.

In the apparatus based on this method, the scanning head and the processing tool must have a large number of degrees of freedom to ensure the requisite facility of use and control. This is a serious disadvantage, because it requires a very complex mechanical construction that must at the same time meet high standards of accuracy. Further, because of the mutual effects of the various degrees of freedom, simple means of adjustment are no longer adequate to compensate tool tolerances in such an instrument. This results in further inaccuracies attributable to tool changes during processing.

In this method, the removal of the temporary inlay from the tooth, the method of shaping the dental replacement, the manner in which the template is fitted in its mount, and the scanning process itself all demand a high degree of skill in the operator. The results are subject to considerable quality fluctuations and often demand a very large amount of time.

Another known method, similar to that described above, is described in EP-B-0 267 227. This makes use of an automatic scanning process similar to that used in profile-milling machines. For this purpose, a hydraulic valve is switched by surface contact and controls a drive system that moves the hydraulic valve and the processing tool in accordance with the surface profile. This arrangement does not meet the required standards of accuracy and is not suitable for practical use in dentistry. Inaccuracies occur in the operation of the hydraulic valve, because static friction of the movable tip requires the application of excessive force for scanning. To eliminate static friction, it is suggested that the movable tip be set to rotate. This is technically impossible because of the mobility required and would reduce by only an insignificant amount the force required at the movable tip, because, when the surface to be scanned rotates, the forces that occur act mainly tangentially upon the tip and thus cause friction between the movable tip and the walls of the drilled guide hole. In addition, the rotating tip could easily damage the original. Finally, because of the pressures that typically occur in hydraulic systems, only a press fit or special se&ling systems can prevent the hydraulic fluid leaking from at the hydraulic valve. Either of these produces friction and hence require still more force to move the tip.

Moreover, the operation of this type of hydraulic valve is subject to relatively large hysteresis. Also, the operation of hydraulic valves is extremely progressive and the force required to move the processing tool is not very great. This results in a strong tendency for the control loop to vibrate, which can be controlled only by appropriate damping and thus requires greater force to operate the valve. Further, hysteresis as such produces further inaccuracies. Finally, use of a hydraulic system makes the system described extremely complex and expensive.

The use of gears cannot achieve a permanently precise, smooth synchronous rotation of original and copy. Errors due to slip, slack, and rough running of the gears cumulate with those of the hydraulic valve and hydraulic system.

The required angle for proper functioning, between the tip and the processing tool on the one hand and the axis of rotation of the original and the copy on the other, calls for a sharply pointed processing tool of small circumference. The speed at the processing tool's center of rotation is zero. At the high running speeds required for this type of processing tool, the tool's useful life in this type of arrangement is not long enough for the production of a single inlay, for example of ceramic material. In particular, the lack of a means of supplying cooling lubricant makes it impossible to process hard materials or remove large amounts of material.

The angle referred to above also limits the usefulness of this arrangement, particularly for the production of inlays. Thus, for example, the side wall of an inlay and the steep sides of a box-type cavity preparation remain inaccessible for the tip and the processing tool.

In the arrangement described in the publication last referred to, the processing tool and the sensor head may have different shapes. Differences of shape in the processing tool and the sensor head reduce copying accuracy, particularly when shapes have a distinct surface form or texture, as in the case of an inlay. In practice, the high speed of rotation of the shaped mass, at about 1'000 rpm, makes it impossible to produce distinct forms or textures because of the finite acceleration of the scanning and process-tracking system. In particular, the inertia of the sensor's mass limits to very low values the maximum acceleration that the scanning and process-tracking systems can achieve.

SUMMARY OF THE INVENTION

The object of the present invention is to propose a method and an apparatus that permit the dentist and/or dental technician to make dental replacements with a highly accurate fit in a single session in accordance with normal dental practice and at low cost, but which do not suffer from the disabilities described in the prior art referred to above.

The object of the present invention is achieved by an apparatus for making dental replacements such as inlays, onlays and crowns and the like by scanning a template. The apparatus comprises a template holder which is rotatable about a first axis of rotation for rotating and holding a template resembling the dental replacement. A blank holder rotatable about a second axis of rotation is held in spaced relationship from the first axis of rotation for rotating and holding a blank to be processed into a dental replacement. A sensor is mounted to detect the contour of a template on the template holder as it rotates and produces an output signal in response to the contours. A processing tool is mounted a fixed distance from the sensor to make contact with and process a blank on the blank holder in accordance with the contour detected by the sensor. A synchronized rotary drive means rotates the template holder and a template thereon relative to the sensor and simultaneously rotates the blank holder and a blank template thereon by the same amount relative to the processing tool. A processing means connected with the sensor and the processing tool moves the sensor and tool relative to the template and the blank respectively by controlled amounts in response to the output signal of the sensor. The present disclosure describes the invention by reference to an inlay, but it is analogously applicable to onlays. Its main features are as follows:

Inlays can be made economically, like amalgam fillings, in a single session; the ingredients used are safe and reliable materials; the inlays are of high aesthetic worth and have a long useful life.

The method and apparatus described in the present disclosure make it possible to achieve an accuracy of fit within a tolerance of only a few thousandths of a millimetre and use a scanning force of only a few millinewton, namely of less than 300 millinewton.

Because of the high accuracy of fit obtainable, the gap between the tooth and the inlay is narrower than the critical size that allows caries to form.

The temporary inlay is readily removable without risk of damage to the tooth or the need of further treatment.

Because only very little scanning pressure is necessary for the copying process and this pressure is constant—the typical mean scanning pressure is only about 50 millinewton—the residual elasticity of the soft temporary inlay produces only slight, irrelevant dimensional aberrations.

Because the scanning pressure is so slight, the retaining pin for the temporary inlay can be attached by adhesive only.

Before the filling material has set firmly and while it is still soft, it allows the temporary inlay's masticatory surface to be shaped.

The inlay can be made so accurately that it needs little or no corrective work when it is fitted.

The dentist can use established techniques to make the temporary inlay, hence the amount of retraining required for the entire production process is reduced to a minimum.

The shape of the sensor head is exactly the same as that of the processing tool, hence the track of the processing tool in the substrate mass is exactly the same as that of the sensor used to scan the surface of the temporary inlay.

The combination of two different tools at the same time permits the removal of substantial amounts of material from the blank, yet makes it possible to take into account extremely small prominences and depressions of only a few thousandths of a millimetre in the manufacture of the inlay. The separation of preliminary and fine processing greatly increases both the useful life of the tools and their long-term accuracy. In fact, if without this separation into two process cycles or if tools intended only for fine processing were used, the useful life of the processing tools Would be too short when they are used on hard substrate materials such as ceramics and would make their economical, practical use impossible.

The proposed rotation-synchronizer system is absolutely free from slip or slack, rotates true, remains absolutely centered, is perfectly rigid and resistant to wear, and thus no true-running or synchronization errors can occur or cause copying errors.

Several typical embodiments of the present disclosure are described in detail by reference to the drawings, as follows:

BRIEF DESCRIPTION OF THE DRAWINGS

FIG. 2d is a side view of a further embodiment of the sensor described in FIG. 2a;

FIG. 2f is a typical embodiment with a special sensor described in FIG. 2a;

DETAILED DESCRIPTION OF THE PREFERRED EMBODIMENTS

Figure 1:
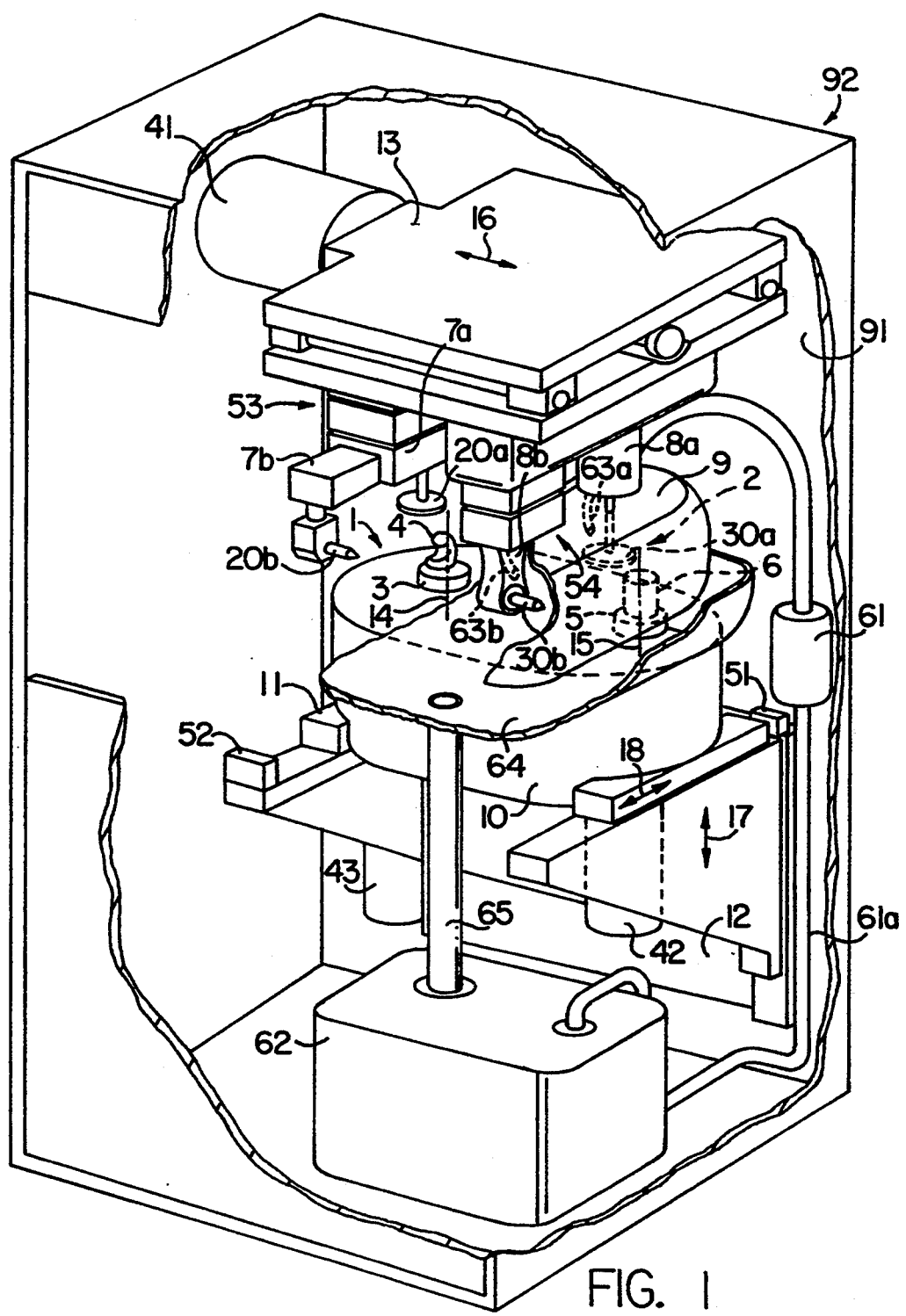
FIG. 1 is a perspective view of the apparatus described in the present disclosure.

In FIG. 1, 1 is a side for an original and 2 is a side for a copy. The original side 1 has a template-holder unit 3 to hold the temporary inlay 4, the copy side 2 has a substrate-holder unit 5 to hold a blank in the form of a substrate mass 6. In addition, first and second contact-sensitive sensors 7a, 7b are provided on the original side 1, and first and second processing systems 8a, 8b are provided on the copy side 2. A hood 9 covers the copy side 2 to prevent cooling lubricant from contaminating the apparatus. The hood also provides protection from pieces of material thrown off during processing. The template-holder unit 3 and the substrate-holder unit 5 are fitted on a rotation-synchronizer system 10 driven by a rotary drive 42 which ensures that they rotate synchronously. A slide system 11 attached to an elevator system 12 operated by an elevator drive 43 guides the rotation-synchronizer system 10. The sensors 7a, 7b and the processing systems 8a, 8b are fitted to a linear stage 13 which can be moved by means of a drive 41. 20a and 20b are sensor heads of the sensors 7a, 7b; 30a and 30b are processing tools of the processing systems 8a, 8b. The first sensor head 20a and the first processing head 30a are exactly the same shape, likewise the second sensor head 20b and the second processing head 30b. When they are fitted in place, their respective position relative to the temporary inlay 4 and the substrate mass 6 is identical. The shape of-the two processing tools 30a, 30b is so chosen as to permit the shaping of practically any surface form and texture when the tools are used in combination, and at the same time to give the processing tools a long operating life. For this purpose the first processing tool 30a has a relatively large surface and a narrow cutting width. The shape of the second processing tool 30b along its rotational axis is pointed.

The center-to-center distance of the sensor heads 20a, 20b and of their respective processing tools 30a, 30b is equal to the distance between the rotational axes 14, 15 of the template-holder and substrate-holder units 3, 5 respectively. The height of the first sensor head 20a relative to the first processing tool 30a is equal to the height of the second sensor head 20b relative to the second processing tool 30b. The respective directions of movement of the linear stage 13 and the elevator system 12 are perpendicular to each other, as shown by arrows 16, 17, and the movement of the linear stage 13 is parallel to a plane defined by the rotational axes 14, 15. 51 is a first stop and 52 a second stop for the slide system 11 and thus also for the rotation-synchronizer system 10, whose direction of movement is shown by an arrow 18. The stops 51, 52 respectively determine the first and second positions of the slide system 11 and thus also of the rotation-synchronizer system 10, so that in the first position the centers of the first sensor head 20a and of the first processing tool 30a and in the second position the centers of the second sensor head 30a and of the second processing tool 30b preferably lie in the plane defined by the rotational axes 14, 15.

A first means of adjustment 53 is provided for adjusting the positions of the sensor heads 20a, 20b relative to the rotation-synchronizer system 10. The means of adjustment 53 has two degrees of freedom in a plane perpendicular to the direction of the elevator movement 17, of which one degree of freedom is parallel with the linear movement 16 and the other is perpendicular thereto. A third degree of freedom of the means of adjustment 53 is parallel to the direction of the elevator movement 17. The degree of freedom parallel to the linear movement 16 is of special importance, because this degree of freedom makes it possible to alter the size relationship of the copy to the original. In practice, this degree of freedom is available for optimizing the accuracy of fit, hence the means of adjustment for this degree of freedom is readily accessible, for example by means of a micrometer screw not shown on the drawing.

A second means of adjustment 54 is provided for adjusting the second processing tool 30b, and for this purpose the second processing tool 30b is fitted on the second means of adjustment 54. The degrees of freedom of the means of adjustment 54 are in a plane perpendicular to the direction of the elevator movement 17. Further, the degrees of freedom are parallel to the direction of linear movement 16 and the direction perpendicular thereto. This means of adjustment is available for adjusting the height of the second processing tool 30b relative to that of the second sensor 7b. These relative heights must be the same as the relative heights of the first sensor 7a to the first processing tool 30a. Thus a third degree of freedom is parallel with the elevator movement.

A means of supplying cooling lubricant has a pump 61 which aspirates cooling lubricant by a pipe 61a from a tank 62. The pipe 61a is connected to nozzles 63a, 63b which supply the cooling lubricant to the processing tools 30a, 34b. A drain pipe 65 connects the tank 62 to a collecting sump 64; the collecting sump 64 collects the used cooling lubricant and returns it to the tank 62.

A housing 92 accommodates the elevator system 12, the linear stage 13, and the cooling-lubricant supply system; the elevator system 12 and the linear stage 13 are attached to a rear wall 91 of the housing 92 and the tank 62 of the cooling-lubricant supply system is attached to the floor of the housing 92.

Figure 2A:
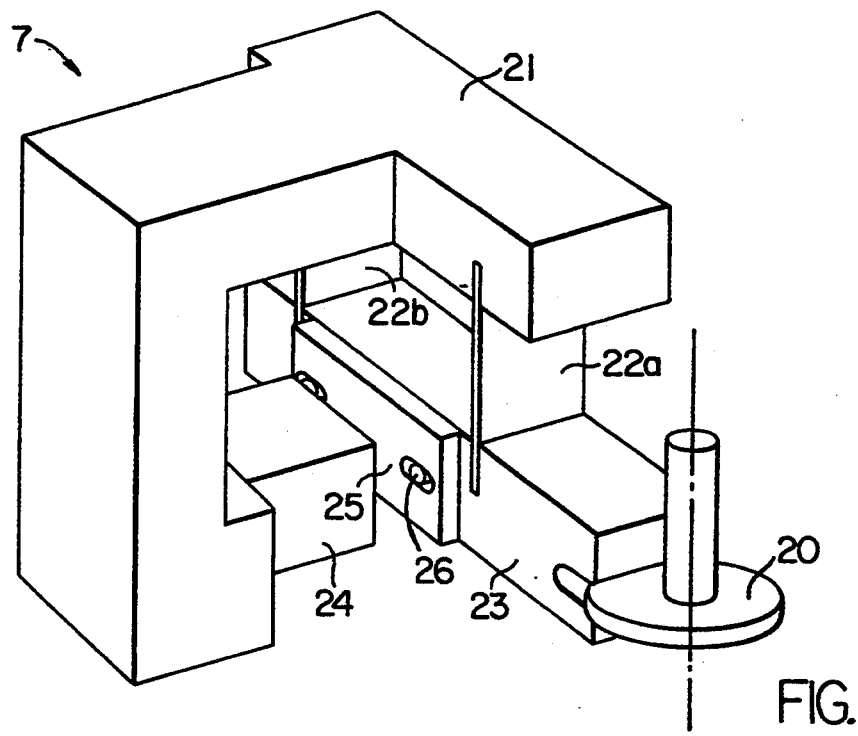
FIG. 2a is a perspective view of a first embodiment of a sensor of the apparatus described in FIG. 1.

As shown in FIG. 2a, the sensor 7a has a stator 21 fitted to a sensor holder not shown on the drawing. First and second flexible mounts 22a, 22b connect a head carrier 23 to the stator 21 in such a manner as to permit the head carrier 23 to move; a preferred embodiment of such a mount is a spring plate 22a; 22b . A sensor head 20a is provided on the side of the head carrier 23 that faces the temporary inlay 4 (FIG. 1). The sensor head 20a detects the periphery of the temporary inlay 4 and has the same shape as the processing tool opposite. In particular, the radii of curvature, thickness, tool shaft, and the position of the fitted sensor head 20a are identical to those of the processing tool. A Hall element 24 attached to the stator and at least one magnet 25 fitted to the head carrier 23 on a slide system 26 form a distance-measuring system. When a force acts on the sensor head 20a, it displaces the head carrier 23 in relation to the stator 21 and thus the position of the magnet 25 relative to the Hall element 24. The voltage this produces at the output of the sensor 7a is proportional to the deflection of the sensor head 20a from its no-load position. The slide system 26 permits balancing the voltage of the sensor 7 in the no-load position.

Figure 2B:
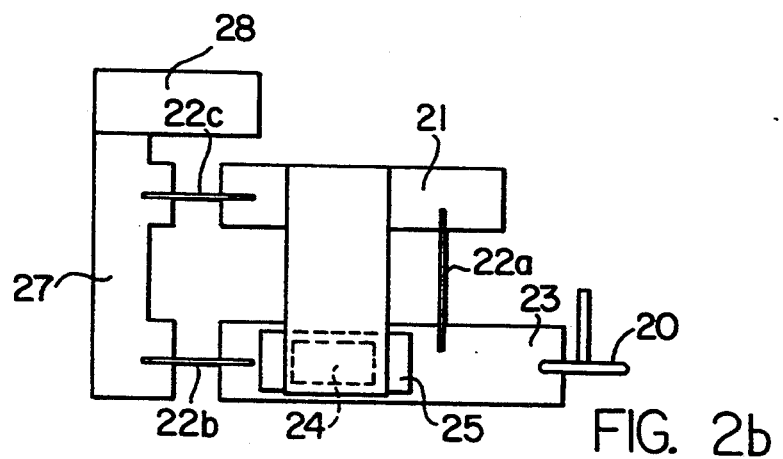
FIG. 2b is a side view of a sensor of a second embodiment of a sensor of the apparatus described in FIG. 1.

In FIG. 2b, 28 is a mass-compensator element attached to a compensator arm 27. On the one hand the compensator arm 27 is suspended from the stator 21 by a third flexible mount 22c which allows it to rotate, and on the other it is connected to the head carrier 23 by the second flexible mount 22b. The mass moment of inertia of the mass-compensator element 28 relative to the rotational axis formed by the third flexible mount 22c corresponds to that of the head carrier 23 and the lower portion of the compensator arm 27. As the sensor's motion accelerates, the mass inertia of the head carrier 23 opposes the accelerated motion. The sensor head 20a and the head carrier 23 tend to move in opposition to the accelerated motion. At the same time, the accelerating force also acts on the mass-compensator element and the mass inertia is compensated; the mass moments of inertia are equal and opposite, and prevent displacement of the head carrier 23 and the sensor head 20a relative to the stator 21 that would otherwise result from this acceleration. Because the sensor is made insensitive to acceleration, the acceleration that the linear system can achieve is practically unlimited. This is important for fast scanning of surface irregularities.

Figure 2C:
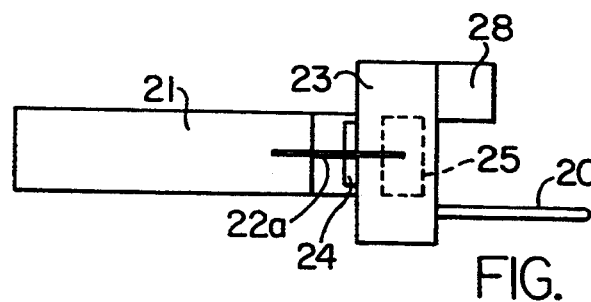
FIG. 2c is a plan view from above of a further embodiment of a sensor of the apparatus described in FIG. 1.

As shown in FIG. 2c, the mass-compensator element 28 is fitted directly to the head carrier 23, which is attached to the stator 21 by means of the first flexible mount 22a in such a manner as to compensate the mass moments of inertia that occur due to the sensor's accelerated motion. This embodiment has the advantage that it reacts to any forces that act laterally and/or longitudinally. This typical embodiment is thus particularly suitable for the use of pointed sensor heads which are often subjected to lateral forces caused by rotary motion when a temporary inlay is being scanned.

The sensor shown in FIG. 2c can be used with one of the electronic or optical sensors shown in FIG. 2a or 2b to act as a two-sensor system, in which the sensor shown in FIG. 2c is used as the second sensor 7b shown in FIG. 1 and the sensor shown in either FIG. 2a or 2b is used as the first sensor 7a.

Figure 2D:
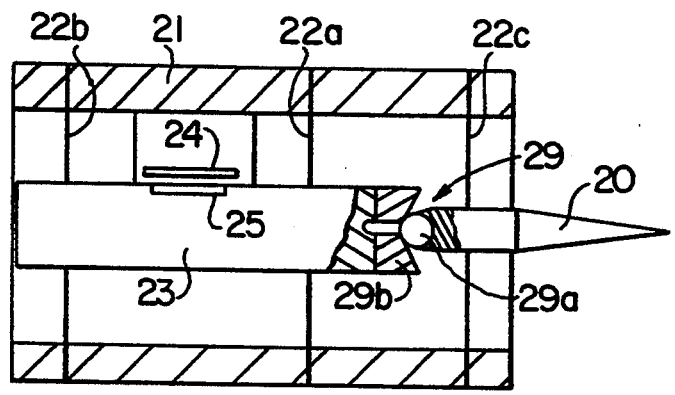

FIG. 2d shows a typical embodiment of a sensor that responds both laterally and longitudinally. This embodiment has a stator 21 and a head carrier 23 carried on a first spring-type element 22a and a second spring-type element 22b. A third spring-type element 22c holds the sensor head 20a so as to form the universal joint 29 described below, which connects the sensor head 20a to the head carrier 23.

The universal joint 29 consists of a ball 29a and a seating 29b attached to the front of the head carrier 23 and the sensor head 20a. The side of the seating 29b that faces the ball 29a preferably has a conical depression at whose lowest point the ball 29a assumes a stable, unambiguous, slack-free position in which the contact area between the ball 29a and the conical seating 29b is circular. When a force acts longitudinally on the sensor head 20a, the magnet 25 attached to the head carrier 23 moves in relation to the Hall element 24. When a force acts laterally on the sensor head, it causes elongation of the universal joint; the ball is displaced laterally relative to the seating 29b and the annular contact surface between the ball 29a and the seating 29b becomes a point. This contact point is preferably displaced outward from the center of the conical surface of the seating. The angle of the conical surface is so chosen that when the ball 29a is displaced from its lowest position in the seating 29b, it produces a displacement of the head carrier and thus an elongation of the universal joint 29. The sliding properties of the ball 29a and the seating 29b and the smoothness of their surfaces must meet very stringent standards; for example, the ball 29a and its seating 29b should be preferably made of sapphire or diamond.

Figure 2E:
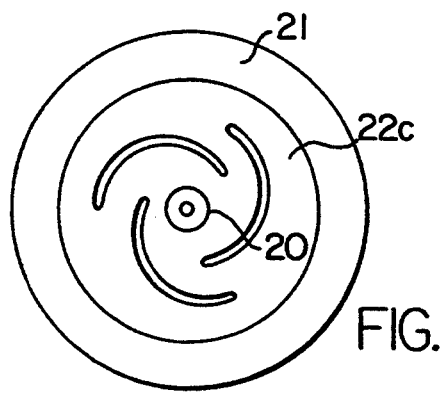
FIG. 2e is a plan view from above of the sensor described in FIG. 2d.

The first and second spring-type elements 22a, 22b must have a high lateral-to-longitudinal stiffness ratio, in order to prevent lateral displacement of the head carrier when a lateral force acts on the head carrier. A preferred embodiment of the shape of the first and second spring-type elements 22a, 22b resembles a short, flat spiral spring, as shown in FIG. 2e, and the head carrier 23 is attached to the centers thereof. The metal guides of these elements are so designed that any load applied is evenly distributed over the entire surface of the spring-type element. The first and second spring-type elements may also be made of flat or C-shaped spring plates attached on the one hand to the stator and on the other to the head carrier.

The third spring-type element 22c allows the sensor head 20a to be tilted in any direction about its point of attachment to the third spring-type element 22c, and permits the longitudinal displacement of the sensor head 20a with an equally slight effort. At the same time, the lateral stiffness of the third spring-type element is considerable. The shape of the third spring-type element 22c is the same as that of the first and second spring-type elements. The sensor head is attached to its center. The third spring-type element 22c may also be made as a corrugated membrane or as a corrugated membrane reduced by partial removal of material.

Figure 2F:
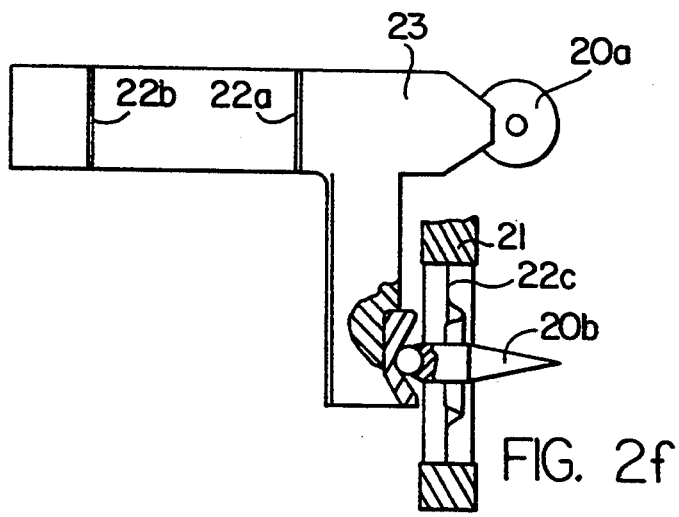

FIG. 2f shows a typical embodiment of a combined sensor with two sensor heads 20a, 20b. In this embodiment, therefore, only one distance-measuring system is necessary, because the head carrier carries both the sensor heads 20a, 20b. The mode of functioning is similar to that of one of the embodiments described above.

When spring-type elements are used in the typical embodiments described above, there is no static friction, the sensors work at a mean applied force of less than 300 millinewton, for example at about 25 millinewton. At the same time they have good dynamic properties, with a typical rise and fall time of only a few milliseconds. In addition, the measuring sensitivity is high, with a resolution of a few thousandths of a millimetre.

An optical or induction-type distance-measuring system may be used for the sensor instead of a system that consists of a Hall element 24 and a magnet 25.

Figure 3A:
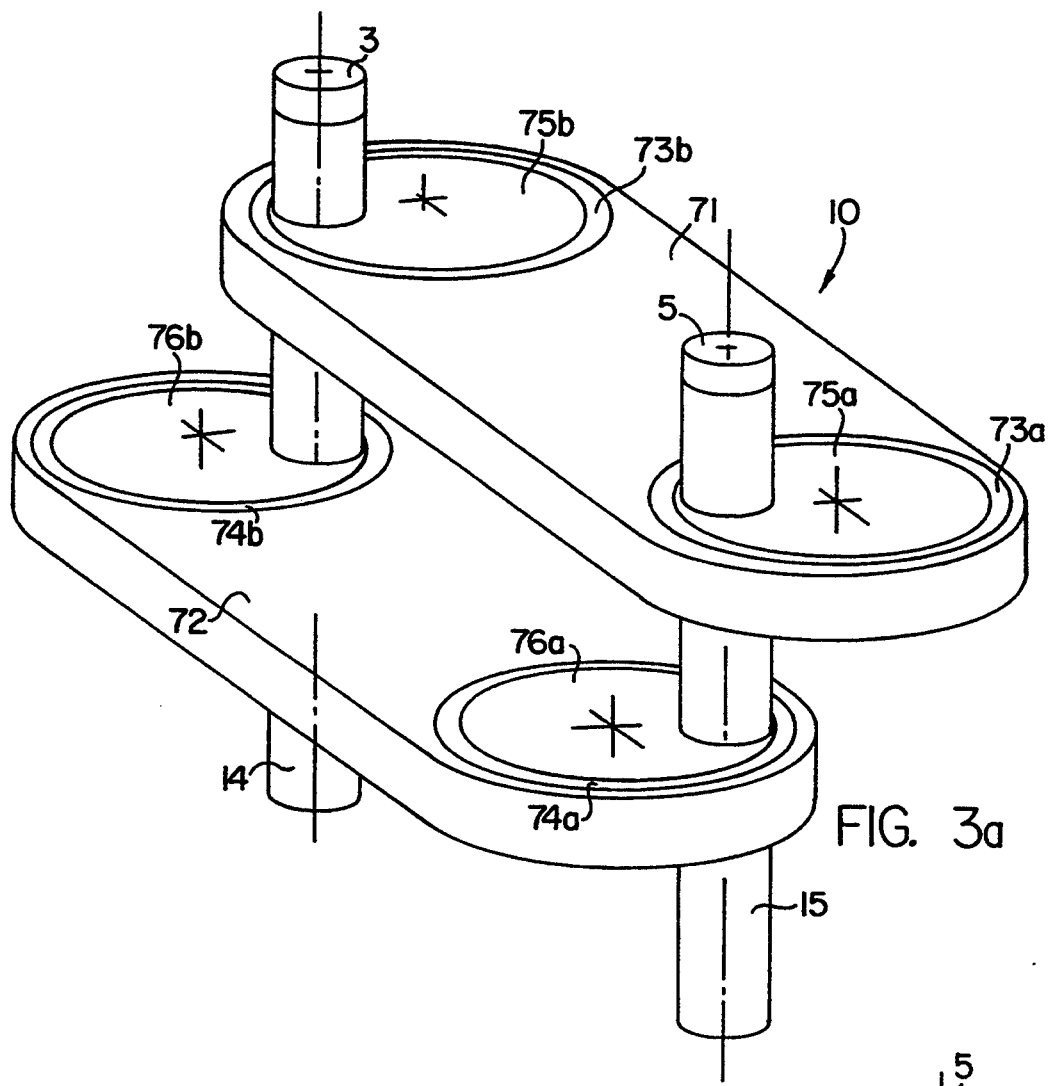
FIG. 3a is a perspective view of the principal components of a first typical embodiment of the rotation-synchronizer system of the apparatus described in FIG. 1.

In FIG. 3a, 71 and 72 are synchronizer rods that transfer the torque from one rotating shaft 15 driven by the rotary drive 42 (FIG. 1) to the other rotating shaft 14. The substrate-holder unit 5 fits on one end of one of the rotating shafts 15 and the template-holder unit 3 fits on one end of the other rotating shaft 14 (FIG. 1). The rotating shafts 14, 15 run in bearings (not shown in greater detail) in the housing of the rotation-synchronizer system 10 (FIG. 1). At both their ends the synchronizer rods 71, 72 are connected to the rotating shafts by bearing elements 73a, 73b, 74a, 74b and by disks 75a, 75b, 76a, 76b inserted therein. The centers common to the bearing elements and the disks are eccentric relative to the rotating shafts 14, 15; the upper disk 75a and the lower disk 76a are made of one piece of material with the rotating shaft 15, and the upper disk 75b and the lower disk 76b are made out of one piece of material with the rotating shaft 14. Preferably, each center of the upper disks 75a, 75b forms a right angle with the center of the respective lower disks 76a, 76b relative to the rotating shafts 14 and 15 (FIG. 3c). This ensures that when one of the synchronizer rods 71, 72 is in the dead-center position, the other synchronizer rod 72, 71 transfers the maximum torque, hence in the dead-center position the center of the bearing elements 73a, 73b and 74a, 74b of a synchronizer rod 71, 72 lie in the same plane as the rotating shafts 14, 15. This ensures the reliable, perfect transfer of torque regardless of the angle of rotation.

Figure 3B:
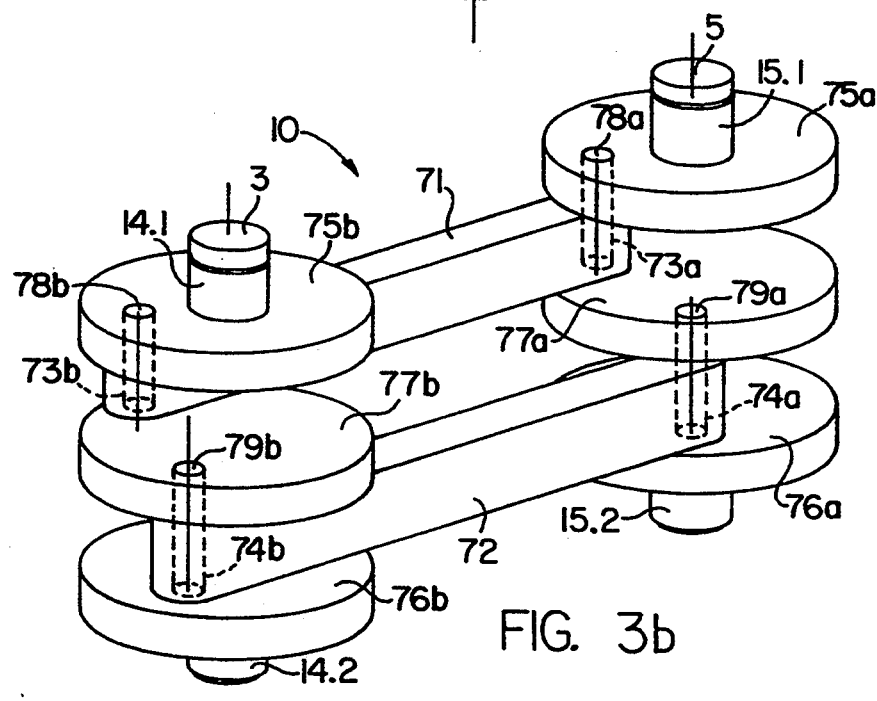
FIG. 3b is a perspective view of the principal components of a second typical embodiment of the rotation-synchronizer system.
Figure 3C:
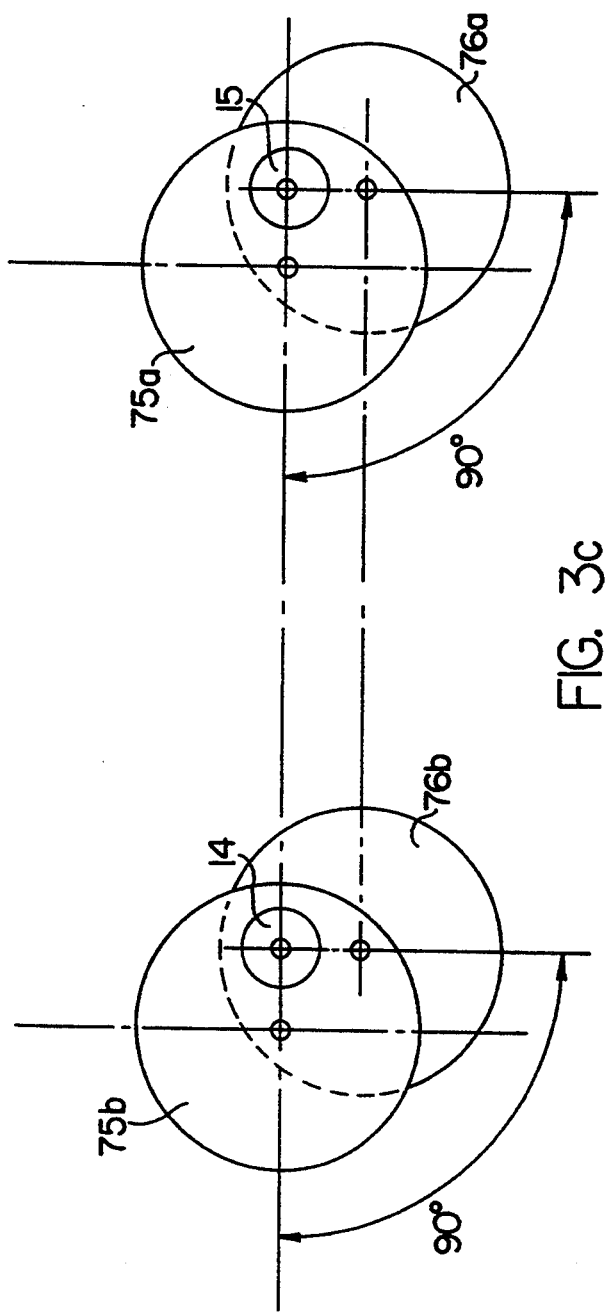
FIG. 3c is a diagrammatic drawing which shows the rotation-synchronizer system in a particular position.

FIG. 3b shows intermediate disks 77a, 77b between the upper disks 75a, 75b and the lower disks 76a, 76b. The upper disks 75a, 75b are fixed to the sections 15.1, 14.1 of the rotating shafts, and the lower disks 76a, 76b to the sections 15.2, 14.2, and each of the disks is concentric relative to the center of the respective section of the rotating shafts 14.1, 14.2 and 15.1, 15.2. Bolts 78b, 79b provide the mechanical connection between sections 14.1, 14.2 of the rotating shaft, and bolts 78a, 79a that between sections 15.1, 15.2. The bolts are eccentric on the disks and are connected to the sections of the rotating shafts 14.1, 14.2 and 15.1, 15.2; preferably, the centers of bolts 78b, 79b form a right angle with the centers of the sections of rotating shaft 14.1, 14.2, and the centers of bolts 78a, 79a likewise form a right angle with the centers of sections 15.1, 15.2. The synchronizer rod 71 forms mobile joints with the bolts 78a, 78b by means of the bearing elements 73a, 73b; the synchronizer rod 72 likewise forms mobile joints with the bolts 79a, 79b by means of the bearing elements 74a, 74b.

The processing system 8 is attached to the linear stage by means of a processing-system mount 170 in so movable a manner that when the radial force applied to the processing system 8 exceeds a given maximum, it releases the processing system 8, and processing stops.

Figure 3D:
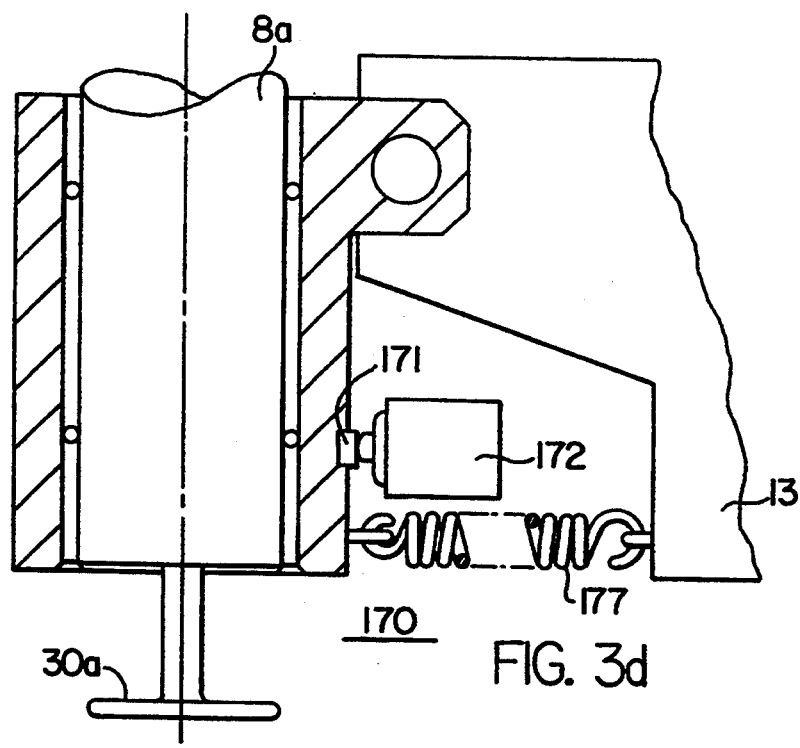
FIG. 3d shows a typical embodiment of a processing-unit holder.

FIG. 3d shows a typical embodiment of a processing-system mount 170. In this embodiment, the processing system 8 has pivot bearings. A spring 177 presses the processing system 8 against an adjustable stop 171 on the side of the processing system 8 that faces the substrate mass 6. The processing system 8 is linked mechanically to a switch 172. If the force effectively applied to the processing tool 30a exceeds a given maximum, the switch 172 opens. This causes processing to stop and the linear stage 13 moves back to its home position.

Figure 3E:
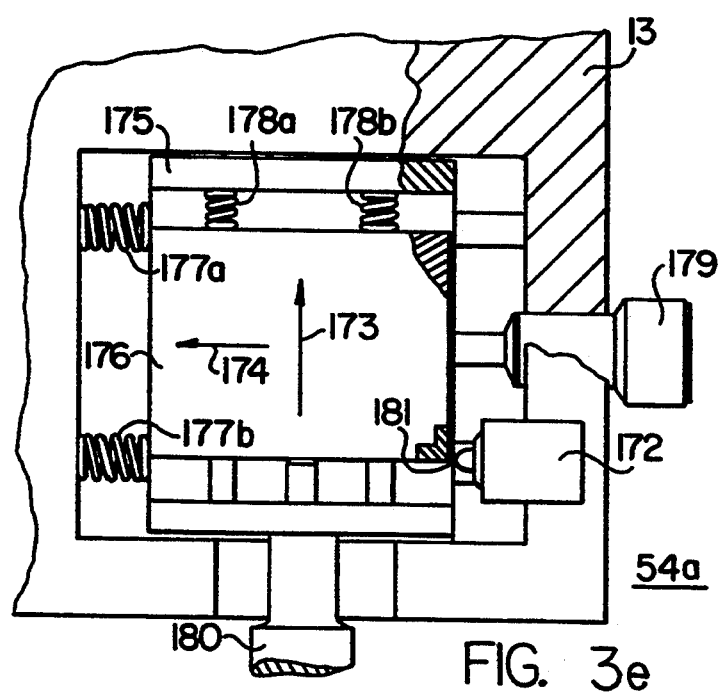
FIG. 3e shows a typical embodiment of a processing-unit holder for the fine-processing section shown in FIG. 3d.

The typical embodiment of a processing-system mount shown in FIG. 3e reacts to excessive force applied radially 173 and tangentially 174 to the processing tool 30. In this embodiment, the processing system 8 is attached to a sliding XY stage 54a that permits the two-dimensional adjustment of the processing system 8. The sliding XY stage 54a consists of an upper sliding stage 175 and a lower sliding stage 176. The upper sliding stage 175 is connected to the sliding linear stage 13.

The processing system 8 is attached to the lower sliding stage 176. Spring-type elements 177a, 177b and 178a, 178b press the upper sliding stage 175 and the lower sliding stage 176 respectively against an adjustment screw 179, 180 opposite. The switch 172 is so placed relative to an adjustable stop 181 in the angle between the two adjustment screws 179, 180 that the switch opens if either the upper or the lower sliding stage 175, 176 is moved, and thus stops the systems. This processing-system mount is particularly suitable for fine, finger-shaped types of processing tools.

Figure 4A:
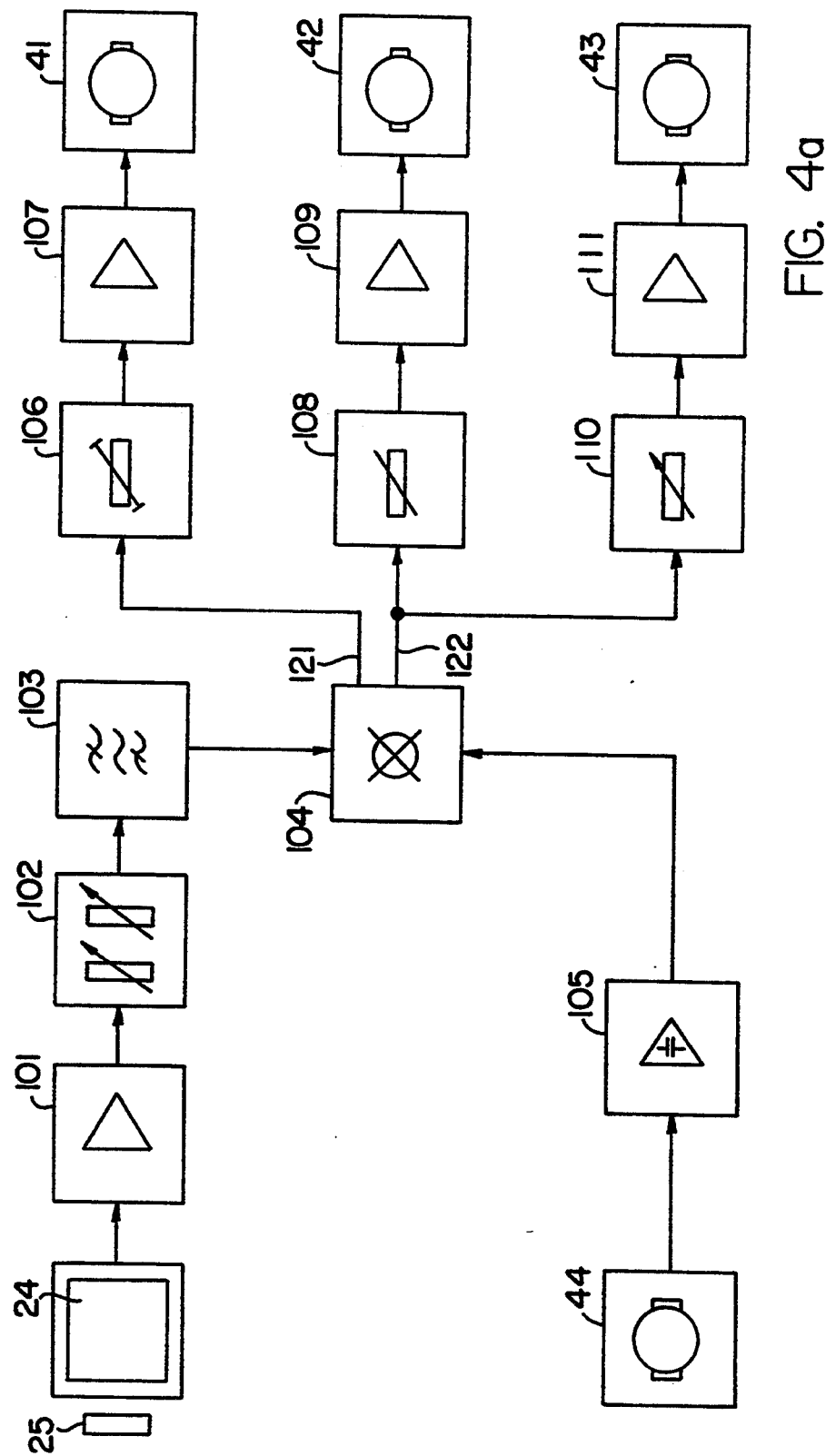
FIG. 4a is a block diagram of an electronic control circuit of the apparatus described in FIG. 1.

FIG. 4a shows the output of the Hall element 24 (FIG. 2a) connected to a preamplifier 101. Downstream of the preamplifier 101 are a signal-regulator stage 102 and a stop-filter stage 103. The output of the stop-filter stage 103 is connected to an electronic coordinator system 104.44 is the drive of the processing systems 8a and 8b (FIG. 1). It is connected to an electronic milling-system monitor 105 whose output is in turn connected to the electronic coordinator system 104. A first output 121 of the electronic coordinator system 104 is connected to a linear signal processor 106. Downstream of this is a linear power-driver stage 107 which permits control of the drive 41 for the linear stage 13 (FIG. 1). A second output 122 of the electronic coordinator system 104 is connected to a rotary regulator stage 108. A rotary driver stage 109 downstream of this is connected to the rotary drive 42 (FIG. 1). The second output 122 is also connected to an elevation regulator stage 110, downstream of which there is an elevator driver stage 111 and an elevator drive 43 (FIG. 1).

Figure 4B:
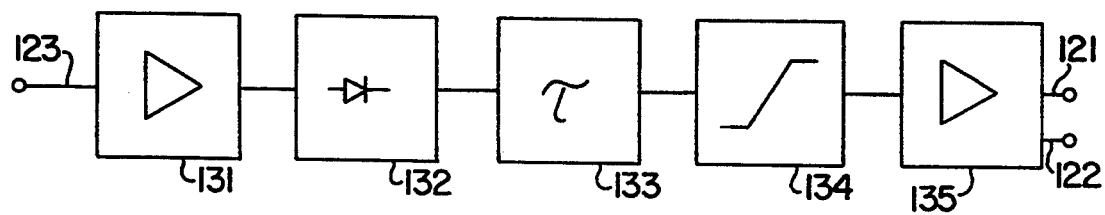
FIG. 4b is a detail of FIG. 4a and describes an electronic-coordinator system.

FIG. 4b shows the principal components of a typical embodiment of such an electronic coordinator system. The processed sensor signal goes via an input 123 to a first matching amplifier 131. From the output of the first matching amplifier, the signal goes to a precision rectifier stage 132; this is a full-wave rectifier that produces the absolute value of the sensor signal. When the sensor is in the home position, the sensor voltage is zero, and a voltage proportional to the sensor's deflection from its home position is produced at the output of the precision rectifier stage 132, regardless of whether the deflection is positive or negative. When the output voltage from the precision rectifier stage 132 is greater than a given maximum, a maximum-value stage 134 transmits a signal to a driver stage 135 which then reduces the speed of the elevator and rotation motors. A time-lag device 133 attenuates unwanted frequencies of the sensor signal.

Figure 4C:
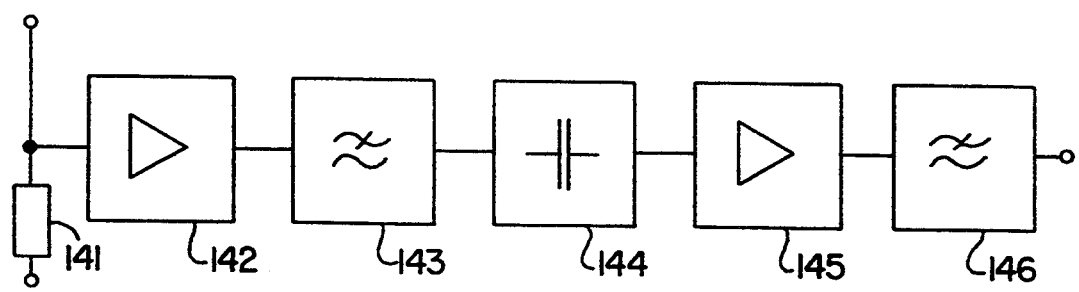
FIG. 4c is a further detail of FIG. 4a and describes a typical embodiment of an electronic milling-system monitor.

FIG. 4c shows the principal components of a typical embodiment of an electronic milling-system monitor. In this, a shunt resistance 141 generates a voltage proportional to the processing tool's output or current consumption. A first amplifier stage 142 amplifies this voltage via the shunt resistance 141. A first low-pass filter stage 143 attenuates the high-frequency components from the processing tool's drive motor. A differentiator stage 144 differentiates the signal. The differentiated signal, which is now proportional to changes in the processing tool's output, is amplified in a second amplifier stage 145 to the values required by the electronic coordinator system. In addition, a second filter stage 146 suppresses the frequency components produced by the drive motor. Efficient attenuation of the frequency components produced by the drive motor is essential, because the amplitudes of these unwanted frequencies can be higher than the detectable changes in the output due to the load. In this typical embodiment, the steep filter characteristic is obtained from two filter stages in series. This is desirable, in order to process as broad a signal spectrum as possible, and this in turn ensures a rapid response from the electronic milling-system monitor.

The following two examples describe respectively how a temporary inlay and an inlay are made in accordance with the apparatus described above.

Operational summary

First of all, the dentist removes in a known manner the affected dental material. Then, the prepared cavity in the tooth is filled with temporary inlay material that hardens on exposure to light. While the filling material is still soft, the masticatory surfaces can be preshaped. After hardening of the temporary inlay material by exposure to light, the material has a rubbery consistency and can thus be readily removed from the prepared dental cavity. The temporary inlay 4 made in this manner has the precise shape of the dental material previously removed. EP-B1-0 195 224 gives a detailed description of a suitable material for temporary inlays.

Figure 5A:
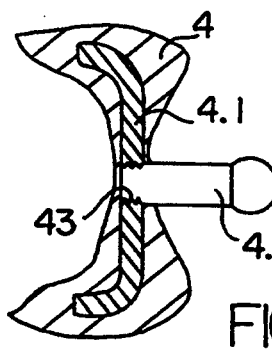
FIG. 5a shows a temporary inlay with a built-in support.

To simplify removal of the temporary inlay 4 from the prepared tooth and to reduce material shrinkage (cf FIG. 5a), a support 4.1 can be embedded in the temporary inlay. The support 4.1 has a handle 4.2 with a thread 4.3 for screwing it into the support 4.1. The shape of the support 4.1 is such as to fit into the prepared cavity. Various prefabricated shapes of support are available to suit different sizes of tooth and of prepared cavity. The shape of the support 4.1 reduces material shrinkage in the temporary inlay 4, particularly along its major axis. Before removal of the temporary inlay 4 from the prepared cavity, the handle 4.2 is removed from the support 4.1. The support itself is preferably made of a material that transmits light. After removal of the handle 4.2, the masticatory surface of the tooth can be preshaped. When the material of the temporary inlay has hardened, it can be finally shaped while it is still in the tooth, and because it is still relatively soft after it has hardened, it can be finished with tools that remove the material but do not damage the tooth. The handle 4.2 is then again screwed into the support 4.1 and the temporary inlay 4 removed from the prepared cavity. The handle 4.2 facilitates the reliable removal of the temporary inlay 4 from the prepared cavity. For further processing, the handle 4.2 is then removed from the temporary inlay 4 and the hole in the temporary inlay 4 for the handle 4.2 is closed.

Figure 5B:
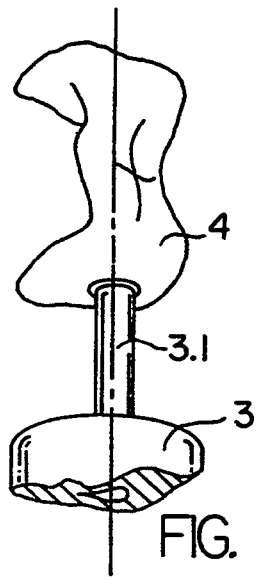
FIG. 5b shows a temporary inlay as described in FIG. 5a, prepared for scanning and secured by adhesive to a support.

The temporary inlay 4 is attached by means of a retaining pin 3.1 (FIG. 5b) to its holder unit 3 on the original side 1 (FIG. 1). For this purpose, because the contact pressure applied for scanning the template 4 is only very slight, the retaining pin 3.1 may simply be attached by a suitable adhesive to a surface of the temporary inlay or, if the template lacks a suitable surface, a hole may bet drilled in the temporary inlay and the retaining pin inserted in the hole.

Figure 5C:
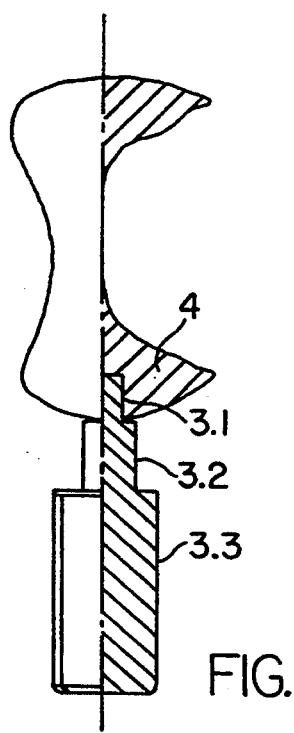
FIG. 5c shows a temporary inlay as described in FIG. 5a, prepared for scanning and secured by a hole to a support.

FIG. 5c shows a typical embodiment of a retaining pin 3.1 suitable for attachment by means of a drilled hole. This retaining pin 3.1 has a stepped shaft, with a first step 3.2 and a second step 3.3. The diameter of the retaining pin 3.1 is so dimensioned as to fit into the template-holder unit 3 without slack, i.e. as a sliding fit. The diameter of the second step should correspond to that of a standard drill and provide a press fit in the hole in the temporary inlay 4. The diameter of the first step corresponds to that of the stump formed in the substrate mass 6 at the lower end of the copy inlay. The diameter of the first step should be kept as small as possible, but must be large enough to ensure that during processing the copy inlay does not accidentally break off at the stump under the load of the processing tool 30. Typically, the diameter of the first step might be 3 mm, that of the second step 1.5 mm.

On the copy side 2, the substrate mass 6, whose color should match the material of the tooth, is attached to the substrate-holder unit 5 (FIG. 1), and the substrate mass 6 is attached to a substrate holder (not shown) that ensures precise and stable positioning of the substrate mass 6 on the substrate-holder unit 5 during processing.

Figure 5D:
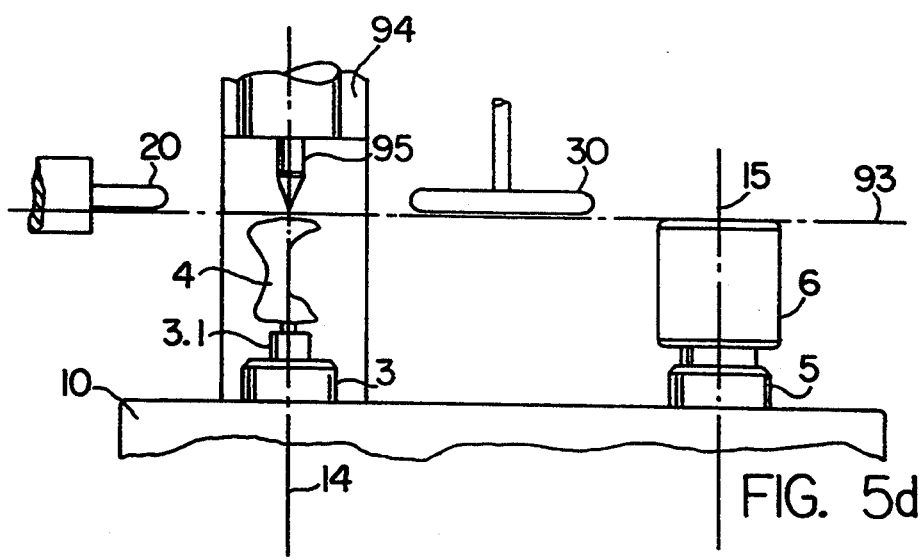
FIG. 5d is a typical example of how a temporary inlay may be fitted in the system.

The description which now follows refers to FIG. 5d for the method of fitting the temporary inlay 4 and the substrate mass 6 to their respective holder units 3, 5. To determine the appropriate height at which the temporary inlay 4 should be fitted on the template-holder unit 3, a guide pin 95 is provided on the original side 1; this guide pin 95 lies on the rotational axis 14 of the template-holder unit 3 and can be moved back and forth along this axis. Preferably, the guide pin 95 should be attached to a guide slide 94 whose guide is connected to the rotation-synchronizer system 10. On the original side 1, the home position of the tip of the guide pin 95 facing the template-holder unit 3 marks the upper edge of the substrate mass 6. The tip of the guide pin 95 should be slightly above the level of the upper edge 93 of the substrate mass 6. For better accessibility in fitting the temporary inlay 4, the tip of the guide pin 95 is moved away from the template-holder unit 3 and the retaining pin 3.1 is inserted in the template-holder unit 3. The tip of the guide pin 95 is returned to its initial position and the temporary inlay 4 is moved closer to the tip of the guide pin 95 until the gap between the upper edge of the temporary inlay 4 and the tip of the guide pin 95 is less than the thickness of the processing tool 30 or the sensor head 20. The retaining pin 3.1 is then fixed in this position in the template-holder unit 3.

At this height, the processing tool 30 comes into contact with the substrate mass 6 only shortly before the sensor head 20 first touches the temporary inlay 4. Immediately after the processing tool 30 reaches the upper edge of the substrate, it starts to form the permanent inlay from the substrate mass 6. By appropriate positioning of the tip of the guide pin 95, the temporary inlay 4 can be set at a level that allows the best possible use to be made of the substrate mass 6 and requires the removal of a minimum amount of material. Further, the tip of the guide pin 95 guides the sensor head 20 and the processing tool 30 before the sensor head 20 reaches the temporary inlay 4 and before the processing tool 30 reaches the substrate mass 6, each on its respective rotational axis 14, 15. When the sensor head 20 first comes into contact with the temporary inlay 4 and the processing tool first touches the substrate mass 6, the tip of the sensor head 20 is near the rotational axis 14 of the temporary inlay 4 and the tip of the processing tool 30 is near the rotational axis 15 of the substrate mass 6.

Figure 6A:
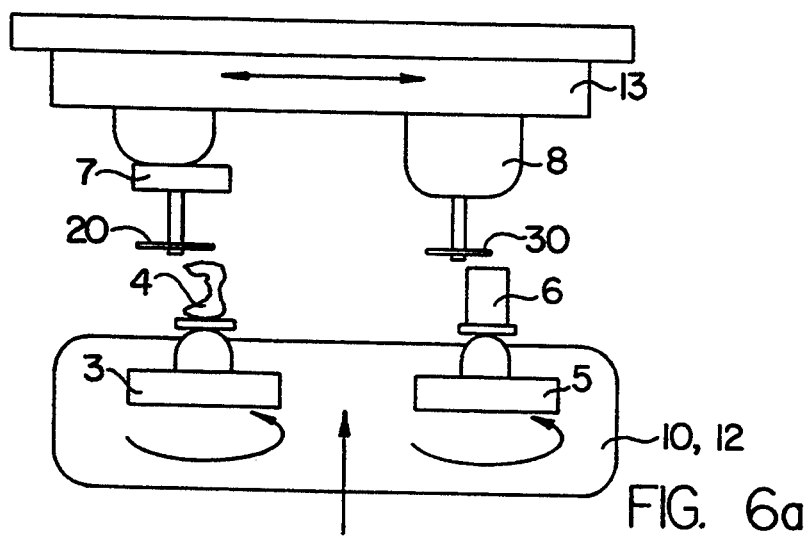
FIG. 6a, 6b and 6c are a simplified diagrammatic representation of the process of making an inlay.

Processing starts with the feed phase (FIG. 6a). In this, the processing tool 30, the template-holder unit 3, and the substrate-holder unit 5 all rotate, the elevator system 12 raises the rotation-synchronizer system 10, and the linear stage 13 is moved to its starting position.

During processing (FIG. 6b), the temporary inlay 4 and the substrate mass 6 perform a combined elevation and rotation movement, so that an imaginary point on the substrate mass and on the edge of the temporary inlay describes a screw-like movement. When the linear stage 13 is moved, the sensor head 20 and the processing tool 30 can be moved any distance from the rotational axes 14, 15 of the template-holder and substrate-holder units 3, 5. As the sensor head 20 scans the temporary inlay 4, the information from the sensor 7 is transmitted to the drive 41 of the linear stage 13 in such a manner as to ensure that the sensor head 20 applies a constant pressure to the surface of the temporary inlay 4 while it remains in contact therewith. Thus, the sensor 7 and hence the linear stage 13 with the processing system 8 scan the exact surface form of the temporary inlay 4. Because the shapes of the sensor head 20 and the processing tool 30 are exactly the same, the processing tool 30 reproduces in the substrate mass 6 exactly the same surface features that the sensor head 20 scans on the temporary inlay 4.

In the final phase (FIG. 6c), processing ends when the sensor reaches the support for the temporary inlay 4.

Figure 6B:
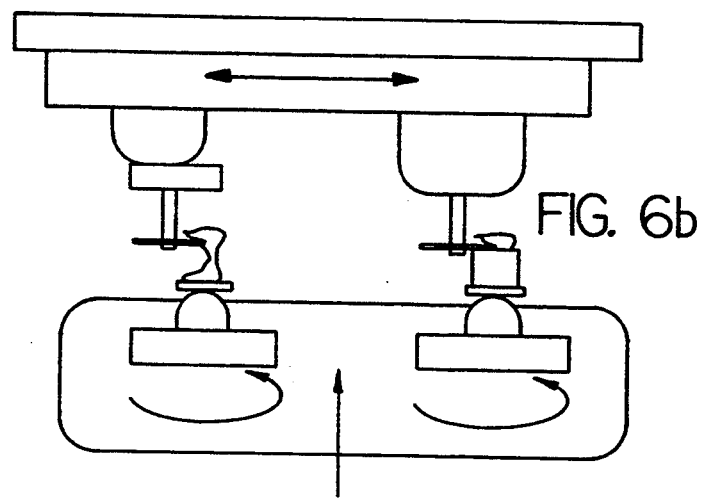
Figure 6C:
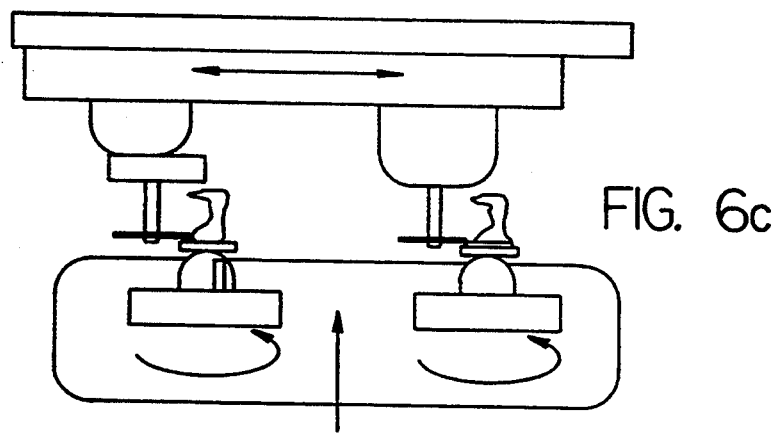

For a still more accurate fit, the processing operation shown in FIGS. 6a to 6c and described above can be repeated by a second processing run in which a finer processing tool is used.

The finished inlay is then removed from the copy side 2. After appropriate cleaning, the inlay is ready for insertion in the prepared dental cavity, where it is then cemented into place and polished. The inlay is made so accurately that in most cases an exact fit is obtainable at once, without the need for subsequent reworking or corrective work.

In a second typical procedure, the temporary inlay 4 is produced on an impression. For this purpose, the dentist uses a known procedure to make an impression of the tooth to be prepared, and then passes the impression to a dental technician or an assistant for further processing. The dental technician or assistant makes a temporary inlay 4 on this impression. For this purpose, the temporary inlay 4 is provided with a retaining pin, as described above, and fitted in the apparatus.

This method has the advantage that the dentist need only make an impression in a known manner and the dental technician can shape the temporary inlay; the dentist then only has to check that the inlay fits properly before cementing it into place.

When the apparatus is used for the automatic production of an inlay, the output signal from the sensor 7 is transmitted to the preamplifier 101 in the electronic control circuit (FIG. 4a). As described in greater detail below, the signal-regulator stage 102 placed downstream in the signal path makes it possible to adjust the sensor's no-load voltage and the scaling of the sensor's signal voltage. As likewise described in greater detail below, the stop-filter stage 103 suppresses unwanted frequencies in the signal spectrum. Thus processed, the sensor-signal voltage goes to the electronic coordinator system 104 which is also supplied with the output signal from the electronic milling-system monitor 105. The rotary regulator stage 108 (FIG. 4b) also makes it possible to adjust the rate of deceleration. The sensor-signal voltage transmitted by the first output 121 of the electronic coordinator system 104 from the linear signal processor 106 is inversely proportional to the deflection of the sensor head 20 from its home position. Speed add direction of the linear drive 41 are proportional to the input voltage of the linear signal processor 106. When the sensor head 20 is in its home position, the no-load voltage is available at the sensor's output. When the no-load voltage is available at the input of the linear signal processor 106, the linear drive 41 moves the sensor 7 toward the temporary inlay 4. When the sensor head 20 touches the temporary inlay 4, deflection occurs and, for example, the voltage increases at the output of sensor 7. This voltage increase slows down the motion of the linear drive 41. At a given nominal deflection, the linear drive 41 is stopped. The servo system thus formed always resets to precisely this home or no-load position. In the home position, the sensor head 20 and the processing tool 30 are in the same position relative to their respective rotational axes 14, 15. Because of this servo system and because the sensor head 20 and the processing tool 30 are the same shape, the processing tool 30 copies the exact path of the sensor head 20 over the surface of the temporary inlay 4.

As shown in FIG. 1, the sensor 7 and the processing tool 20 are rigidly linked to each other via the linear stage 13. During processing, noise from bearings and the mechanical processing of the substrate mass 6 cause considerable vibrations. These vibrations are transmitted to the sensor 7, where they produce a microphone effect and are amplified in the servo system. Because only a small amount of force is necessary to keep the sensor head 20 in contact with the temporary inlay and because of the high resolution of measured distance that the sensor 7 possesses, these vibrations can produce an interference signal whose amplitude may be much greater than the scanning signal itself. The frequency spectrum of the interference signals depends on the speed at which the processing system rotates. In this spectrum, peaks occur at the running-speed frequency and at all multiples of that frequency. These peaks occur in a frequency range where there are signal components of the scanning signal, hence these interference signals cannot be eliminated by a reduction in the response time of the sensor 7. To eliminate the interference frequencies, the filter stages are designed aS notch-type stop filters that have a narrow notch whose center frequency is equal to the frequency of the processing system's running speed and its multiples. These produce a frequency response in the sensor electronics that mirrors the spectrum of the interference signals.

As height differences on the surface being scanned increase, the distance that the linear stage 13 has to travel likewise increases. When there are sharp edges in the surface shape, the linear stage 13 may no longer be able to track the surface shape, because its speed is finite. As it scans the surface, the sensor may lift off or apply an unacceptably strong force. Either condition leads to errors, and the latter may damage the temporary inlay 4.

The electronic coordinator system 104 has the task of preventing these errors by keeping the sensor deflection constantly within proper limits. Because the sensor deflection is proportional to the sensor-signal voltage, this voltage must not be less than a given minimum nor exceed a given maximum. When the sensor-signal voltage reaches these limits, the electronic coordinator system 104 sends a signal to the second output 122. This reduces the speeds of rotation and elevation by the required amount until the sensor-signal voltage returns within the permitted range. The rate of deceleration of the elevation and rotation speeds is adjustable in the elevation-regulator stage 110 and the rotary regulator stage 108 respectively.

Because of the high maximum speeds that are possible in linear motion, the processing tool may be subjected to unacceptably high loads during processing. This can happen when there are large amounts of material to be removed. Hence, to protect the processing tool, the electronic milling-system monitor 105 continually measures the processing system's output. To ensure that the electronic milling-system monitor 105 remains insensitive to fluctuations in the processing system's output due to ageing or dimensional differences of the processing tool, it generates an intermediate signal which is proportional to the differential of the processing system's output. A signal appears at the output of the electronic milling-system monitor 105 as soon as the value of this intermediate signal exceeds a given maximum. This signal is then transmitted to the electronic coordinator system 104, where it causes the linear, rotation, and elevation movements to slow down. Slowing down by the required amount continues until the processing system's power consumption returns within the permitted range.

When an inlay is made in two consecutive processing runs, each processing run is performed as described above by reference to FIGS. 6a to 6c which apply to making an inlay in a single processing run. In a first processing run, the rotation-synchronizer system 10 is in the first position defined by the first stop 51 of the slide system 11 (FIG. 1). In this position, the first processing tool 30a makes the approximate profile of the inlay. In this process it removes most of the excess material. Because the first processing tool has a narrow cutting width, it can produce sharp edges in the direction in which the substrate mass 6 rotates. The first processing run ends when the elevator system 12 completes its upward movement over the entire length of the temporary inlay 4. The linear stage 13 moves back to its home position and the slide system 11 moves to its second position, defined by the second stop 52. It makes the second processing run in this position, but for this purpose the elevator system 12 should now preferably move down. The second processing run can be at different elevation and rotation speeds from those used in the first run.

The second processing tool 30b used in the second processing run produces the fine details on the inlay surface. In this run, the amount of material that has to be removed is usually small, hence the force applied to the substrate mass 6 is also small. The second processing tool 30b is sharply pointed and can thus be used to form slight depressions, angled grooves, and dimples in the surface parallel to the direction in which the substrate mass 6 rotates.

Instead of two sensors 7a, 7b and two processing systems 8a, 8b, the apparatus may have only a single sensor 7 and a single processing system 8, as already described by reference to FIGS. 6a to 6c.

A particularly simple inlay or one that demands less stringent accuracy may be made in a single processing run by means of the first processing tool 30a. FIG. 6 shows that an apparatus which has only a single processing tool needs fewer working parts. In particular, such an apparatus can dispense with a slide system 11, a second sensor 20b, a second processing tool 30b, and the means of adjustment 54 associated with the second processing tool 30b, and the first means of adjustment 53 needs only two degrees of freedom perpendicular to the elevator movement 17.

A system with a single processing tool 30b may also be a feasible solution for applications where softer substances are used, such as synthetic materials. If these materials are reasonably soft, a single tool with a correspondingly small surface has a sufficiently long useful life. Such a system can dispense with the first sensor 20a, the first processing tool 30a, the slide system 11, and the second adjustable stage 54, and the first adjustable stage 53 similarly needs only two degrees of freedom perpendicular to the elevator movement.

I claim:

1. Apparatus for making dental replacements such as inlays, onlays and crowns and the like by scanning a template comprising:

a template holder rotatable about a first axis of rotation for rotating and holding a template resembling a dental replacement;

a movable blank holder rotatable about a second axis of rotation in spaced relationship from the first axis of rotation for rotating and holding a blank to be processed into a dental replacement;

a sensor mounted to detect the contours of a template on the template holder and producing an output signal in response to the contours;

a processing tool mounted a fixed distance from the sensor to make contact with and process a blank on the blank holder;

a synchronized rotary drive means for rotating the template holder and a template thereon relative to the sensor and simultaneously rotating the blank holder and a blank thereon by the same amount relative to the processing tool, the synchronized rotary drive means having:

two upper and two lower sections of rotating shaft, each upper section of rotating shaft being rigidly connected to an upper disk, and each lower section of rotating shaft being likewise rigidly connected to a lower disk;

intermediate disks between the upper and lower disks;

the upper, lower, and intermediate disks being concentric relative to their respective sections of rotating shaft;

the upper disks being connected to the intermediate disks by first bolts and the intermediate disks being in turn attached by second bolts to the lower disks;

the first and second bolts being eccentric in relation to the sections of rotating shaft, and the center of each first bolt on an upper disk and the center of each second bolt on a lower disk being disposed 90° from one another about their respective sections of rotating shaft; and two synchronizer rods the one synchronizer rod forming mobile joints with the first bolts by means of first bearing elements, and the other synchronizer rod likewise forming mobile joints with the second bolts by means of second bearing elements; and a processing means connected with the sensor and the processing tool for moving the sensor and tool relative to the template and the blank respectively by controlled amounts in response to the output signal of the sensor.

2. Apparatus for making dental replacements such as inlays, onlays and crowns and the like by scanning a template comprising:

a template holder rotatable about a first axis of rotation for rotating and holding a template resembling a dental replacement;

a movable blank holder rotatable about a second axis of rotation in spaced relationship from the first axis of rotation for rotating and holding a blank to be processed into a dental replacement;

a sensor mounted to detect the contours of a template on the template holder and producing an output signal in response to the contours;

a processing tool mounted a fixed distance from the sensor to make contact with and process a blank on the blank holder;

a synchronized rotary drive means for rotating the template holder and a template thereon relative to the sensor and simultaneously rotating the blank holder and a blank thereon by the same amount relative to the processing tool; and a processing means connected with the sensor and the processing tool for moving the sensor and tool relative to the template and the blank respectively by controlled amounts in response to the output signal of the sensor, the processing means including means for reducing the speed of movement of the sensor and processing tool relative to one another when a predetermined level of the output signal of the sensor is exceeded.

3. Apparatus as defined in claim 2, wherein:

the synchronized drive means includes one rotatable shaft connected to rotate the rotatable template holder and another rotatable shaft connected to rotate the rotate the blank holder synchronously with the template holder.

4. Apparatus as defined in claim 3, wherein:

the synchronized drive means has upper and lower synchronizer rods connected at each end to the respective rotating shafts by means of bearing elements and eccentric upper and lower disks secured to each shaft; and the centers of the upper eccentric disks on the rotating shafts are disposed about the shaft axes 90° from the centers of the lower disks.

5. Apparatus for making dental replacements such as inlays, onlays and crowns and the like by scanning a template comprising:

a template holder rotatable about a first axis of rotation for rotating .and holding a template resembling a dental replacement;

a movable blank holder rotatable about a second axis of rotation in spaced relationship from the first axis of rotation for rotating and holding a blank to be processed into a dental replacement;

a sensor mounted to detect the contours of a template on the template holder and producing an output signal in response to the contours;

a processing tool mounted a fixed distance from the sensor to make contact with and process a blank on the blank holder;

a synchronized rotary drive means for rotating the template holder and a template thereon relative to the sensor and simultaneously rotating the blank holder and a blank thereon by the same amount relative to the processing tool;

a processing means connected with the sensor and the processing tool for moving the sensor and tool relative to the template and the blank respectively by controlled amounts in response to the output signal of the sensor;

the sensor including a Hall element producing the sensor output signal, and the processing means which receives the output signal having a preamplifier which has a signal-regulator stage and a stop-filter stage downstream for processing the output signal and an output connected to an electronic coordinator system and wherein the processing system additionally includes:

a drive connected to an electronic milling-system monitor whose output is connected to the electronic coordinator system;

a first output from the electronic coordinator system which has a linear power-driver stage downstream to control the drive for a linear drive stage producing the driving forces for moving the sensor and the tool linearly;

a second output from the electronic coordinator system connected to a rotary regulator stage that has a rotary driver stage downstream which is connected to the synchronized rotary drive means; and the second output being connected to an elevation-regulator stage that has an elevation-driver stage downstream which is in turn connected to elevator drive means for raising and lowering the template holder and the blank holder.

6. Apparatus in accordance with claim 5, wherein the filter stages of the stop-filter stage are made as notch filters which have a narrow notch whose center frequency is equal to the frequency and multiples thereof of the speed of the processing system.

7. Apparatus in accordance with claim 6, wherein the electronic coordinator system produces a minimum voltage and a maximum voltage;

the electronic coordinator system generates a further signal when the deflection of the sensor produces a proportional sensor-signal voltage of less than the minimum voltage or more than the maximum voltage; and means are provided for modifying the speed of the synchronized rotary drive means and of the elevator drive means when the further signal is produced at the second output, until the sensor-signal voltage returns to the permissible range between the maximum and minimum voltages.

8. Apparatus in accordance with claim 7, wherein the electronic milling-machine monitor generates an intermediate signal proportional to the differential of the power consumption of the processing system and generates a further signal which is transmitted to the electronic coordinator system when the intermediate signal exceeds a given maximum; the further signal causing the linear, synchronized rotary and elevator drive movements to slow down until the power consumption is again within the permissible range.

9. Apparatus for making dental replacements such as inlays, onlays and crowns and the like by scanning a template comprising:

a template holder rotatable about a first axis of rotation for rotating and holding a template resembling a dental replacement;

a movable blank holder rotatable about a second axis of rotation in spaced relationship from the first axis of rotation for rotating and holding a blank to be processed into a dental replacement;

a sensor mounted to detect the contours of a template on the template holder and producing an output signal in response to the contours;

a processing tool mounted a fixed distance from the sensor to make contact with and process a blank on the blank holder;

a synchronized rotary drive means for rotating the template holder and a template thereon relative to the sensor and simultaneously rotating the blank holder and a blank thereon by the same amount relative to the processing tool; and a processing means connected with the sensor and the processing tool for moving the sensor and tool relative to the template and the blank respectively by controlled amounts in response to the output signal of the sensor, the processing means including means for stopping the processing of sensor signals when a predetermined maximum load is exceeded.

10. Apparatus for making dental replacements such as inlays, onlays and crowns and the like by scanning a template comprising:

a template holder rotatable about a first axis of rotation for rotating and holding a template resembling a dental replacement;

a movable blank holder rotatable about a second axis of rotation in spaced relationship from the first axis of rotation for rotating and holding a blank to be processed into a dental replacement;

a sensor mounted to detect the contours of a template on the template holder and producing an output signal in response to the contours;

a processing tool mounted a fixed distance from the sensor to make contact with and process a blank on the blank holder;

a synchronized rotary drive means for rotating the template holder and a template thereon relative to the sensor and simultaneously rotating the blank holder and a blank thereon by the same amount relative to the processing tool;

a processing means connected with the sensor and the processing tool for moving the sensor and tool relative to the template and the blank respectively by controlled amounts in response to the output signal of the sensor and wherein;

the sensor is one of two different sensors mounted on a first support along a first ordinate in spaced relationship from one another;

the processing tool is one of two different processing tools mounted on a second support along a second ordinate parallel to the first ordinate and with the same spaced relationship as the sensors; and slide means are connected to the supports for shifting the sensors and the processing tools relative to the template holder and blank holder respectively to permit the different sensors and tools to make a dental replacement from a blank according to a template.

11. Apparatus as defined in claim 10 further including stops cooperating with the slide means for limiting the shifting movement of the sensors and tools.

12. Apparatus as defined in claim 11, wherein:

the stops are placed to limit the shifting movement of the support for the sensors at positions in which one sensor or the other is aligned with the first axis of rotation of the template holder, and to limit the shafting movement of the support for the processing tools at positions in which one tool or the other is aligned with the second axis of rotation of the blank holder.

13. Apparatus as defined in claim 10, wherein:

the one of the processing tools has a relatively large surface and a narrow cutting width, and the other of the processing tools has a pointed shape.

14. Apparatus as defined in claim 10, wherein:

first means of adjustment is provided for the adjustment of the position of the first and second sensors in relation to the synchronized drive means.

15. Apparatus as defined in claim 14, wherein:

second means of adjustment is provided for the adjustment of the position of one of the processing tools relative to the sensors, the one of the tools is fitted to the second means of adjustment.

16. Apparatus as defined in claim 9, wherein:

the sensor is a low friction sensor having a mean contact pressure less than 300 millinewtons for contacting the template and detecting the template contours.

17. Apparatus as defined in claim 16, wherein:

the sensor has a distance-measuring means that operates substantially friction-free and produces the output signal which represents the contact force.

18. Apparatus as defined in claim 17, wherein:

the distance-measuring means in selected from the group of measuring means consisting of a Hall element, an optical detector and an inductive detector.

19. Apparatus as defined in claim 9, wherein:

the sensor has a head for contacting a template, and the head has the same shape as the processing tool.

20. Apparatus as defined in claim 9, wherein:

a retaining pin is provided on the template holder for holding a template.

21. Apparatus as defined in claim 16, wherein:

the sensor includes a head carrier with one side facing the template holder and a stator connected moveably to the head carrier;

a sensor head is fitted on the one side of the head carrier facing the template holder; and a distance-measuring means is connected with the stator and head carrier for measuring the contact force on a template.

22. Apparatus as defined in claim 21, wherein:

the stator and the head carrier are connected moveably to each other by first and second flexible members.

* * * * *